United States Patent [19]

Eichhorn et al.

[11] Patent Number: 4,983,752

[45] Date of Patent: Jan. 8, 1991

[54] PREPARATION OF ACRYLONITRILE

[75] Inventors: Hans-Dieter Eichhorn, Cleveland; Martin J. Dancey, Middlesbrough, both of Great Britain; Guenter Herrmann, Heidelberg, Fed. Rep. of Germany; James W. Steen, Middlesbrough, Great Britain

[73] Assignee: BASF Chemicals Limited, Cleveland, Great Britain

[21] Appl. No.: 525,309

[22] Filed: May 18, 1990

[51] Int. Cl.$^5$ .......................................... C07C 253/26
[52] U.S. Cl. ..................................................... 558/322
[58] Field of Search .......................................... 558/322

[56] References Cited

U.S. PATENT DOCUMENTS

| | | | |
|---|---|---|---|
| 4,049,575 | 9/1977 | Sasaki et al. | 252/439 |
| 4,409,122 | 10/1983 | Kleuskens et al. | 502/20 |
| 4,709,070 | 11/1987 | Sasaki et al. | 558/322 |
| 4,709,071 | 11/1987 | Sasaki et al. | 558/322 |
| 4,757,038 | 7/1988 | Sasaki et al. | 558/322 |
| 4,774,352 | 9/1988 | Sasaki et al. | 558/322 |

FOREIGN PATENT DOCUMENTS 0057041 10/1985 European Pat. Off.
2560480 1/1987 Fed. Rep. of Germany.

*Primary Examiner*—Joseph Paul Brust
*Attorney, Agent, or Firm*—Keil & Weinkauf

[57] ABSTRACT

Acrylonitrile is prepared by a process which comprises the ammoxidation of propylene with ammonia and molecular oxygen or a gas containing molecular oxygen at from 300° to 600° C. in the presence of a metal oxide catalyst which contains tellurium and one or more of the metals iron, molybdenum and antimony, in a fluidized bed, with regeneration of the catalyst during the reaction by the addition of oxidic tellurium compounds or tellurium compounds which form oxidic tellurium compounds under the reaction conditions, in dissolved or suspended form.

6 Claims, No Drawings

PREPARATION OF ACRYLONITRILE

This application is a continuation of application Ser. No. 228,722, filed on Aug. 5, 1988, now abandoned.

Acrylonitrile is prepared industrially on a large scale by ammoxidation of propylene with ammonia and a gas containing molecular oxygen at from 300° to 600° C. in the presence of a metal oxide catalyst, which contains tellurium, in a fluidized bed. In the course of the reaction, the selectivity with respect to acrylonitrile decreases with increased formation of byproducts as a result of a reduction in the tellurium content of the metal oxide catalyst used. There has therefore been no lack of attempts to regenerate the catalyst and to maintain its activity over a longer period.

German Patent No. 2,560,480 describes a process in which metal oxide catalysts which contain tellurium are impregnated or sprayed with an aqueous solution or suspension of metal oxide and tellurium, dried, and then calcined at from 400° to 850° C. Although catalysts treated in this manner make it possible to increase the selectivity with respect to acrylonitrile in the ammoxidation of propylene, the process has the disadvantage that the catalyst has to be removed from the reaction zone and the regeneration comprises a plurality of stages. In another process, described in European Patent No. 57,041, the regeneration of tellurium-containing metal oxide catalyst is carried out by adding tellurium dioxide in the form of solid particles to the fluidized catalyst. However, this process has the disadvantage that the volatile tellurium dioxide is readily discharged without being deposited on the catalyst, and uniform coating of the catalyst with tellurium dioxide is not ensured.

It is an object of the present invention to regenerate the catalyst present in the fluidized bed without interrupting the reaction in a process for the preparation of acrylonitrile by ammoxidation of propylene, the tellurium compound fed in being easy to meter and uniform coating of the catalyst to be regenerated being ensured.

We have found that this object is achieved by a process for the preparation of acrylonitrile by ammoxidation of propylene with ammonia and molecular oxygen or a gas containing molecular oxygen at from 300° to 600° C. in the presence of a metal oxide catalyst which contains tellurium and one or more of the metals iron, molybdenum and antimony, in a fluidized bed, and regeneration of the catalyst, wherein oxidic tellurium compounds or tellurium compounds which form oxidic tellurium compounds under the reaction conditions are added in dissolved or suspended form to the catalyst during the reaction.

The novel process has the advantage that it allows, in a simple procedure, the activity of the catalyst to be maintained for a longer time and the catalysts to be coated uniformly with oxidic tellurium compounds. The novel process also has the advantages that the fluidization behavior of the catalyst bed is not altered and furthermore the tellurium compounds can be metered easily and precisely.

Starting materials used are propylene, ammonia and molecular oxygen or a gas containing molecular oxygen. Suitable gases containing molecular oxygen contain, in addition to 15–99, in particular 18–80, % by volume of molecular oxygen, inert gases such as nitrogen, carbon dioxide and noble gases. An example of a suitable mixture is air. Advantageously, a molar ratio of molecular oxygen to propylene of from 0.3:1 to 10:1 and a ratio of ammonia to propylene of from 0.1:1 of 5:1 are maintained.

The reaction is carried out at from 300° to 600° C., in particular from 400° to 500° C., advantageously under from 0.5 to 4 bar.

The reaction is carried out in the presence of a metal oxide catalyst which contains tellurium and one or more of the metals iron, molybdenum and antimony, in a fluidized bed. Catalysts containing iron and antimony as well as tellurium in oxide form are preferably used. Advantageously, the catalysts are applied to a carrier, eg. silica, alumina, aluminum silicate, titanium dioxide or a mixture of these. Particularly preferred catalysts are those of the formula $Fe_{10}Sb_aTe_bMe_cX_dO_e$, where Me is one or more of the elements vanadium, molybdenum and tungsten, X is one or more of the elements copper, magnesium, zinc, lanthanum, cerium, aluminum, chromium, manganese, cobalt, nickel, bismuth, tin, phosphorus and boron, a is from 5 to 60, b is from 0.1 to 10, c is from 0.01 to 10, d is from 0 to 20 and e is the number of oxygen atoms which corresponds to the oxides obtained by combining the components described. The tellurium-containing metal oxide catalysts suitable for the fluidized bed have, as a rule, a particle size distribution of from 5 to 200 μm.

The addition of the starting materials to the reaction zone can be carried out in various ways. For example, air can first be introduced into the fluidized bed reactor from below through a distributor system and the catalyst particles thus kept in the fluidized state while propylene and ammonia are fed in, individually or as a mixture, through a separate nozzle system into the reaction zone. In order to ensure optimum mixing, the ammonia/propylene mixture is advantageously fed into the fluidized catalyst bed through a large number of nozzles. It has proven advantageous to arrange the feed for the ammonia/propylene mixture above the air feed.

However, the starting materials can also be fed to the reaction zone by another method. For example, the ammonia/propylene mixture may furthermore be enriched with air or molecular oxygen or contain air or molecular oxygen and can be fed to the reaction zone at various radial planes. In another procedure, ammonia, propylene and air or molecular oxygen are mixed completely and fed to the reaction zone from below, through the distributor system of the base of the fluidized zone, or additionally introduced into the fluidized bed in various radial planes.

The space velocity, defined as the mass of catalyst in g per volume of gaseous starting materials (propylene, ammonia and air or molecular oxygen) in $cm^3$ (at standard temperatures and standard pressure) per second is, as a rule, from 1 to 15, preferably from 2 to 10.

According to the invention, oxidic tellurium compounds or tellurium compounds which form oxidic tellurium compounds under the reaction conditions are added in dissolved or suspended form, in particular in dissolved form, to the catalyst during the reaction.

The solution used in the novel process contains one or more oxidic tellurium compounds, such as orthotelluric acid or telluric acid. Tellurium-containing solutions can also be prepared by dissolving metallic tellurium, tellurium monoxide, tellurium dioxide, or tellurous acid in nitric acid. Another possible method is to dissolve, for example, tellurium metal in hydrogen peroxide.

As a rule, such solutions contain oxidic tellurium compounds in an amount of from 0.05 to 250, in particular from 0.1 to 150, g/l, calculated as tellurium.

In addition, the tellurium-containing solutions can contain other catalytically active substances, which should be added to the catalyst. For example, a molybdenum compound can thus be added to give a molybdenum-containing catalyst. Examples of suitable molybdenum compounds are molybdenum dioxide, molybdenum trioxide, ammonium metamolybdate, ammonium paramolybdate, phosphormolybdic acid, boromolybdic acid and molybdate oxalates. Of course, the amount dissolved depends on the solubility of the compounds used and on the type of solvent.

In another procedure according to the invention, a suspension of an oxidic tellurium compound or of one or more tellurium compounds which form oxidic tellurium compounds under the reaction conditions is added to the catalyst during the reaction. Suspensions of tellurium dioxide, tellurium oxide, tellurium trioxide, orthotelluric acid, telluric acid or tellurous acid are preferably used. The content of tellurium compounds is as a rule from 1 to 200, in particular from 2 to 100, g/l, calculated as tellurium. In addition, the aqueous suspension of tellurium compounds can, if required, also contain other catalytically active substances, for example, in the case of a molybdenum-containing catalyst, molybdenum compounds such as ammonium metamolybdate, ammonium paramolybdate or molybdate oxalates as well as molybdenum dioxide or molybdenum trioxide.

In another possible procedure, the tellurium compounds are in the form of solution and the other additives, such as molybdenum compounds, are present in suspended form, or vice versa.

For the preparation of a stable suspension, it has proven useful to add suspending agents in effective amounts. Examples of suitable agents are surfactants, such as alcohols, polyvinyl alcohols, polyvinylpyrrolidone or polyethylene glycols.

The solution or suspension containing tellurium compounds can be fed in continuously or intermittently. As a rule, the amount is chosen so that the activity of the catalyst is maintained under the selected reaction conditions. Advantageously, from 50 to 200%, in particular from 90 to 150%, of the amount of tellurium originally present in the fresh catalyst are maintained. This can easily be checked by taking catalyst samples from the fluidized bed from time to time and analyzing them and basing the amount of tellurium solution or suspension fed in on this analysis.

Water or nitric acid is preferably used as the solvent or suspending agent. On the other hand, however, it is also possible to use other suitable solvents, such as aqueous ammonia solution, acetonitrile or acrylonitrile, as the solvent.

The solution or suspension containing tellurium compounds is advantageously introduced simultaneously at a plurality of points, in particular where the mixing conditions are optimum. The solution or suspension is advantageously introduced at the same points as the starting materials. It has proven particularly useful if solutions or suspensions which contain tellurium compounds are introduced directly into the fluidized bed.

A substantial advantage of the novel process is that, because of the technically simple manner in which the solution or suspension containing tellurium compounds is introduced into the fluidized bed, even relatively large unexpected losses of tellurium can be compensated without adversely affecting the fluidization behavior of the catalyst or producing an excessively high concentration of inert substances in the reaction, as occurs, for example, if tellurium-containing solids, which may be present on an inert carrier, are fed into the catalyst bed.

The acrylonitrile obtainable by the process of the invention is used, for example, for the preparation of polyacrylonitrile or adipodinitrile.

The Examples which follow illustrate the process according to the invention. In the Examples, parts by weight bear the same relation to parts by volume as that of the kilogram to the liter.

COMPARATIVE EXAMPLE 1

6,350 parts by volume/hour (based on standard conditions) of a gas mixture consisting of propylene, ammonia and air are passed into a fluidized bed of 1,000 parts by weight of a catalyst having the composition $Fe_{10}Sb_{20}Te_{1.36}Cu_{3.2}Mo_{0.56}W_{0.1}O_{67.1}(SiO_2)_{55}$, whose tellurium content has decreased to 88% of the original Value. The gas mixture has a molar ratio of air to propylene of 11.0 and a molar ratio of ammonia to propylene of 1.0. The temperature in the fluidized catalyst bed is 448° C. and the pressure is 2.08 bar.

The gas emerging from the reactor is analyzed by gas chromatography, and the selectivity of acrylonitrile formation and the conversion of propylene and the yield of acrylonitrile are determined. The results are shown in the Table below.

COMPARATIVE EXAMPLE 2

The experiment in Comparative Example 1 is repeated, except that a catalyst having the composition $Fe_{10}Sb_{27.5}Te_{1.27}Cu_{3.6}Mo_{0.5}W_{0.2}B_{0.5}P_{0.1}Zn_{0.5}O_{86.9}(SiO_2)_{50}$ is used. The catalyst still has 94% of its original tellurium content and no longer gives the original yields of desired products after prolonged use.

The results of the test are shown in the Table below.

EXAMPLE 1 (according to the invention)

The experiment in Comparative Example 1 is repeated, except that 10 parts by volume of a solution of ortho-telluric acid in water are also fed to the reactor per 1,000 parts by weight of catalyst per hour, over a period of 14 hours, the solution being prepared by dissolving 12 parts by weight of ortho-telluric acid in 100 parts by volume of water.

The gas emerging from the reactor is analyzed by gas chromatography 48 hours after the ortho-telluric acid-containing aqueous solution has been fed in. The results are shown in the Table.

EXAMPLE 2 (according to the invention)

The experiment in Comparative Example 2 is repeated, except that 10 parts by volume of the solution of ortho-telluric acid in water, according to Example 1, are also fed to the reactor per 1,000 parts by weight of catalyst per hour, over a period of 13 hours.

After 48 hours, the gas emerging from the reactor is analyzed; the results are shown in the Table below.

EXAMPLE 3 (according to the invention)

The experiment in Comparative Example 2 is repeated, except that a suspension of 7.5 parts by weight of tellurium dioxide in 20 parts by volume of water is passed into the reactor per 1,000 parts by weight of catalyst over a period of 2 hours.

After 48 hours, the gas emerging from the reactor is analyzed.

COMPARATIVE EXAMPLE 3

The experiment in Comparative Example 1 is repeated, except that the catalyst described in Comparative Example 2 is employed in the fresh unused state. The Table below shows the results of the test after 48 hours and after 672 hours.

EXAMPLE 4 (according to the invention)

The experiment in Comparative Example 3 is repeated, except that, after about 168 hours, a tellurium-containing solution is additionally fed to the reactor in the course of about 3 hours. The tellurium-containing solution to be fed in per 1,000 parts by weight of catalyst is prepared by suspending 1.9 parts by weight of metallic tellurium powder in 10 parts by volume of water, heating the suspension to about 95° C. and then slowly adding 6 parts by volume of a 35% strength $H_2O_2$-containing aqueous solution. In each case, the addition is repeated about 168 hours after the previous addition of tellurium-containing solution. After a total time-onstream of about 690 hours, the gas emerging from the reactor is analyzed and the yields of desired product are determined. Catalyst samples taken from the reactor show that the tellurium content of the catalyst has increased to about 129%, based on the original content, during this period.

EXAMPLE 5 (according to the invention)

The experiment from Example 4 was repeated, except that the solution to be fed in per 1,000 parts by weight of catalyst is prepared by dissolving 1.85 parts by weight of metallic tellurium powder in a sufficient amount of 45% strength nitric acid and adding water to the tellurium nitrate-containing solution until a volume of 20 parts by volume is obtained. After the end of the experiment, catalyst samples taken from the reactor show that the tellurium content of the catalyst is about 21% higher than the original content.

The results of Comparative Examples 1 to 3 and of the novel Examples 1 to 5 show that a process for the preparation of acrylonitrile by ammoxidation of propylene using a tellurium-containing catalyst can be carried out with constant high yields of desired products if the catalyst is brought into contact with a tellurium-containing solution or suspension in the course of the ammoxidation reaction.

TABLE

|  | Test results | | | | | | | | |
|---|---|---|---|---|---|---|---|---|---|
|  | Comp. Ex. 1 | Comp. Ex. 2 | Ex. 1 | Ex. 2 | Ex. 3 | Comp. Ex. 3 after 48 h | Comp. Ex. 3 after 588 h | Ex. 4 | Ex. 5 |
| Selectivity for acrylonitrile, % | 76.30 | 76.58 | 77.79 | 78.47 | 78.32 | 78.85 | 76.65 | 78.90 | 78.81 |
| Propylene conversion, % | 94.91 | 95.09 | 95.40 | 95.50 | 95.30 | 95.71 | 95.22 | 95.59 | 95.71 |
| Yield of acrylonitrile, % | 72.42 | 72.82 | 74.21 | 74.94 | 74.64 | 75.47 | 72.99 | 75.42 | 75.43 |

We claim:

1. In a process for producing acrylonitrile by the ammoxidation of propylene with ammonia and molecular oxygen or a gas containing molecular oxygen at a temperature of from 300° to 600° C. in the presence of a metal oxide catalyst containing tellurium and one or more of the metals iron, molybdenum and antimony in a fluidized bed, wherein the catalyst is regenerated during the reaction, the improvement which comprises adding to the reaction mixture a solution of oxidic tellurium compounds to regenerate the catalyst.

2. The process of claim 1, wherein a solution of a tellurium compound in water or nitric acid is used.

3. The process of claim 1, wherein the tellurium content of the catalyst is maintained at from 50 to 200% of the original tellurium content.

4. The process of claim 1, wherein the solution which contains oxidic tellurium compounds or tellurium compounds which form oxidic tellurium compounds under the reaction conditions is added directly to the fluidized bed.

5. The process of claim 1, wherein the solution of oxidic tellurium compounds or tellurium compounds which form oxidic tellurium compounds under the reaction conditions, additionally contain molybdenum compounds in dissolved form.

6. The process of claim 1, wherein the catalyst contains iron and antimony oxide in addition to tellurium oxides.

* * * * *